US008696880B2

(12) United States Patent
Beer et al.

(10) Patent No.: US 8,696,880 B2
(45) Date of Patent: Apr. 15, 2014

(54) OXIDIZABLE SPECIES AS AN INTERNAL REFERENCE FOR BIOSENSORS AND METHOD OF USE

(75) Inventors: Greg P. Beer, Cassopolis, MI (US); Huan-Ping Wu, Granger, IN (US); Kin-Fai Yip, Elkhart, IN (US)

(73) Assignee: Bayer HealthCare LLC, Whippany, NJ (US)

( * ) Notice: Subject to any disclaimer, the term of this patent is extended or adjusted under 35 U.S.C. 154(b) by 957 days.

(21) Appl. No.: 10/590,765

(22) PCT Filed: Feb. 4, 2005

(86) PCT No.: PCT/US2005/003622
§ 371 (c)(1),
(2), (4) Date: Aug. 24, 2006

(87) PCT Pub. No.: WO2005/078118
PCT Pub. Date: Aug. 25, 2005

(65) Prior Publication Data
US 2007/0045126 A1   Mar. 1, 2007

Related U.S. Application Data

(60) Provisional application No. 60/542,362, filed on Feb. 6, 2004.

(51) Int. Cl.
*G01N 27/327* (2006.01)
(52) U.S. Cl.
USPC ............ 204/403.14; 204/403.04; 204/403.01; 205/777.5

(58) Field of Classification Search
USPC ............ 204/403.01–403.15; 205/777.5, 778, 205/792
See application file for complete search history.

(56) References Cited

U.S. PATENT DOCUMENTS

| 3,791,933 A | 2/1974 | Moyer et al. |
| 3,791,988 A | 2/1974 | Bauer et al. |
| 3,920,580 A | 11/1975 | Mast ............................. 252/408 |
| 4,572,899 A | 2/1986 | Walker et al. .................. 436/18 |
| 4,729,959 A | 3/1988 | Ryan ............................... 436/14 |
| 4,746,607 A | 5/1988 | Mura et al. |
| 4,890,926 A | 1/1990 | Dosmann et al. ............. 356/369 |
| 5,028,542 A | 7/1991 | Kennamer et al. ............. 436/14 |

(Continued)

FOREIGN PATENT DOCUMENTS

| EP | 0 741 186 | 11/1996 | |
| EP | 0 741 186 B1 | 11/1996 | ............... C12M 1/40 |

(Continued)

OTHER PUBLICATIONS

PCT International Search Report dated Jun. 2, 2005 (Scanned in IFW Aug. 24, 2006).

(Continued)

*Primary Examiner* — Keith Hendricks
*Assistant Examiner* — Kourtney S Carlson
(74) *Attorney, Agent, or Firm* — Nixon Peabody LLP

(57) ABSTRACT

A biosensor (102) for determining the presence or amount of a substance in a sample and methods of use of the biosensor (102) are provided. The biosensor (102) for receiving a user sample to be analyzed includes a mixture for electrochemical reaction with an analyte. The mixture includes an enzyme, a mediator and an oxidizable species as an internal reference.

23 Claims, 10 Drawing Sheets

(56) References Cited

U.S. PATENT DOCUMENTS

| | | | |
|---|---|---|---|
| 5,096,671 A | 3/1992 | Kane et al. | 422/82.07 |
| 5,108,564 A | 4/1992 | Szuminsky et al. | |
| 5,120,420 A | 6/1992 | Nankai et al. | 204/403 |
| 5,128,015 A | 7/1992 | Szuminsky et al. | |
| 5,155,628 A | 10/1992 | Dosmann | 359/640 |
| 5,206,147 A | 4/1993 | Hoenes | |
| 5,262,035 A | 11/1993 | Gregg et al. | |
| 5,264,104 A | 11/1993 | Gregg et al. | |
| 5,288,387 A | 2/1994 | Ito et al. | |
| 5,288,636 A | 2/1994 | Pollmann et al. | |
| 5,320,725 A | 6/1994 | Gregg et al. | |
| 5,321,492 A | 6/1994 | Detwiler et al. | 356/73 |
| 5,356,786 A | 10/1994 | Heller et al. | |
| 5,361,314 A | 11/1994 | Kopelman et al. | 385/12 |
| 5,385,846 A * | 1/1995 | Kuhn et al. | 205/777.5 |
| 5,429,735 A | 7/1995 | Johnson et al. | 204/403 |
| 5,449,898 A | 9/1995 | Dosmann | 250/208.1 |
| 5,477,326 A | 12/1995 | Dosmann | 356/406 |
| 5,518,689 A | 5/1996 | Dosmann et al. | 422/82.05 |
| 5,520,786 A * | 5/1996 | Bloczynski et al. | 204/403.14 |
| 5,545,519 A | 8/1996 | Vadagama et al. | |
| 5,582,697 A | 12/1996 | Ikeda et al. | |
| 5,605,837 A | 2/1997 | Karimi et al. | 436/14 |
| 5,611,999 A | 3/1997 | Dosmann et al. | 422/82.05 |
| 5,620,579 A | 4/1997 | Genshaw et al. | 204/402 |
| 5,627,922 A | 5/1997 | Kopelman et al. | 385/12 |
| 5,628,890 A | 5/1997 | Carter et al. | |
| 5,653,863 A | 8/1997 | Genshaw et al. | 205/777.5 |
| 5,660,791 A | 8/1997 | Brenneman et al. | 422/58 |
| 5,682,884 A | 11/1997 | Hill et al. | |
| 5,695,947 A | 12/1997 | Guo et al. | |
| 5,701,181 A | 12/1997 | Boiarski et al. | 356/446 |
| 5,723,284 A | 3/1998 | Ye | 435/4 |
| 5,755,953 A | 5/1998 | Henning et al. | |
| 5,759,364 A | 6/1998 | Charlton et al. | |
| 5,762,770 A | 6/1998 | Pritchard et al. | |
| 5,798,031 A | 8/1998 | Charlton et al. | 204/403 |
| 5,820,551 A | 10/1998 | Hill et al. | |
| RE36,268 E | 8/1999 | Szuminsky et al. | |
| 6,033,866 A * | 3/2000 | Guo et al. | 435/14 |
| 6,153,069 A | 11/2000 | Pottgen et al. | |
| 6,157,442 A | 12/2000 | Raskas | 356/39 |
| 6,157,472 A | 12/2000 | Eum et al. | 359/18 |
| 6,181,417 B1 | 1/2001 | Dosmann | 356/326 |
| 6,258,229 B1 | 7/2001 | Winarta et al. | |
| 6,272,262 B1 | 8/2001 | Kopelman et al. | 385/12 |
| 6,284,125 B1 | 9/2001 | Hodges et al. | |
| 6,287,451 B1 | 9/2001 | Winarta et al. | |
| 6,294,062 B1 * | 9/2001 | Buck et al. | 204/400 |
| 6,297,697 B2 | 10/2001 | Delano et al. | |
| 6,413,411 B1 | 7/2002 | Pottgen et al. | |
| 6,484,046 B1 | 11/2002 | Say et al. | |
| 6,531,040 B2 | 3/2003 | Musho et al. | 204/401 |
| 6,535,753 B1 | 3/2003 | Raskas | 600/310 |
| 6,565,738 B1 * | 5/2003 | Henning et al. | 205/777.5 |
| 6,599,407 B2 | 7/2003 | Taniike et al. | |
| 6,616,819 B1 * | 9/2003 | Liamos et al. | 204/403.02 |
| 6,636,652 B1 | 10/2003 | Kopelman et al. | 385/12 |
| 6,767,441 B1 | 7/2004 | Cai et al. | |
| 6,841,052 B2 | 1/2005 | Musho et al. | |
| 2001/0000129 A1 | 4/2001 | Raskas | 356/39 |
| 2001/0006149 A1 * | 7/2001 | Taniike et al. | 204/403 |
| 2001/0042683 A1 | 11/2001 | Musho et al. | 204/403 |
| 2001/0052470 A1 * | 12/2001 | Hodges et al. | 205/775 |
| 2002/0139692 A1 | 10/2002 | Tokunaga et al. | 205/777.5 |
| 2002/0185375 A1 | 12/2002 | Wogoman | |
| 2003/0149348 A1 | 8/2003 | Raskas | 600/310 |
| 2004/0007461 A1 | 1/2004 | Edelbrock | |
| 2004/0061841 A1 | 4/2004 | Black et al. | 355/30 |
| 2004/0180444 A1 | 9/2004 | Rannikko et al. | 436/14 |
| 2004/0245121 A1 * | 12/2004 | Nagakawa et al. | 205/777.5 |
| 2004/0253367 A1 | 12/2004 | Wogoman | |
| 2005/0247562 A1 | 11/2005 | Tokunaga et al. | 204/450 |
| 2007/0080073 A1 | 4/2007 | Wu et al. | |
| 2008/0145878 A1 | 6/2008 | Marfurt | 435/14 |
| 2009/0014339 A1 | 1/2009 | Beer et al. | 205/777.5 |

FOREIGN PATENT DOCUMENTS

| | | | |
|---|---|---|---|
| EP | 0 762 112 | 3/1997 | G01N 21/47 |
| EP | 1 156 324 A1 | 11/2002 | G01N 27/327 |
| EP | 0 800 086 B1 | 1/2003 | G01N 33/96 |
| WO | WO 93/21928 A1 | 11/1993 | G01N 31/00 |
| WO | WO 95/13535 A1 | 5/1995 | G01N 31/22 |
| WO | WO 95/13536 A1 | 5/1995 | G01N 31/22 |
| WO | WO 2004/040286 A1 | 5/2004 | G01N 27/26 |
| WO | WO 2005/040407 | 5/2005 | |
| WO | WO 2005/040407 A1 | 5/2005 | C12Q 1/00 |
| WO | WO 2005/045234 A1 | 5/2005 | |
| WO | WO 2005/078118 A1 | 8/2005 | C12Q 1/00 |
| WO | WO 2006/110504 A1 | 10/2006 | C12Q 1/100 |

OTHER PUBLICATIONS

Hall, J.W. et al., "Automated Determination of Glucose using ENZ Glucose Oxidase and Potassium Ferro Cyanide ENA Peroxidase," Analytical Biochemistry, vol. 26, No. 1, 1968, pp. 12-17.

* cited by examiner

OXIDIZABLE SPECIES AS AN INTERNAL REFERENCE FOR BIOSENSORS AND METHOD OF USE

CROSS-REFERENCE TO RELATED APPLICATIONS

This application claims priority to Application No. 60/542,362 filed on Feb. 6, 2004, which is incorporated by reference in its entirety.

FIELD OF THE INVENTION

The present invention generally relates to a biosensor, and, more particularly, to a new and improved biosensor, including an oxidizable species as an internal reference and methods of use of the biosensor, for determining the presence or amount of a substance in a sample.

DESCRIPTION OF THE PRIOR ART

The quantitative determination of analytes in body fluids is of great importance in the diagnoses and maintenance of certain physiological abnormalities. For example lactate, cholesterol and bilirubin should be monitored in certain individuals. In particular, the determination of glucose in body fluids is of great importance to diabetic individuals who must frequently check the level of glucose in their body fluids as a means of regulating the glucose intake in their diets. While the remainder of the disclosure herein will be directed towards the determination of glucose, it is to be understood that the new and improved sensor element and method of use of this invention can be used for the determination of other analytes upon selection of the appropriate enzyme.

Methods for determining analyte concentration in fluids can be based on the electrochemical reaction between the analyte and an enzyme specific to the analyte and a mediator which maintains the enzyme in its initial oxidation state. Suitable redox enzymes include oxidases, dehydrogenases, catalase and peroxidase. For example, in the case where glucose is the analyte, the reaction with glucose oxidase and oxygen is represented by equation:

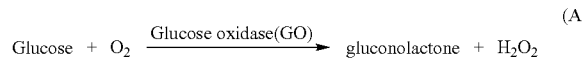

(A)

In the initial step of the reaction represented by equation (A), glucose present in the test sample converts the enzyme ($E_{ox}$), such as the oxidized flavin adenine dinucleotide (FAD) center of the enzyme into its reduced form ($E_{red}$), for example, (FADH$_2$). Because these redox centers are essentially electrically insulated within the enzyme molecule, direct electron transfer to the surface of a conventional electrode does not occur to any measurable degree in the absence of an unacceptably high cell voltage. An improvement to this system involves the use of a nonphysiological redox coupling between the electrode and the enzyme to shuttle electrons between the (FADH$_2$) and the electrode. This is represented by the following scheme in which the redox coupler, typically referred to as a mediator, is represented by M:

Glucose+GO(FAD)→gluconolactone+GO(FADH$_2$)

GO(FADH$_2$)+2M$_{ox}$→GO(FAD)+2M$_{red}$+2H$^+$

2M$_{red}$→2M$_{ox}$+2e$^-$ (at the electrode)

In the scheme, GO(FAD) represents the oxidized form of glucose oxidase and GO(FAD H$_2$) indicates its reduced form. The mediating species $M_{ox}/M_{red}$ shuttles electrons from the reduced enzyme to the electrode thereby oxidizing the enzyme causing its regeneration in situ.

U.S. Pat. Nos. 5,620,579 and 5,653,863 issued to Genshaw et al., and assigned to the present assignee, disclose apparatus and method for determining the concentration of an analyte in a fluid test sample by applying the fluid test sample to the surface of a working electrode, which is electrochemically connected to a counter electrode, and which surface bears a composition comprising an enzyme specific for the analyte. A mediator is reduced in response to a reaction between the analyte and the enzyme. An oxidizing potential is applied between the electrodes to return at least a portion of the mediator back to its oxidized form before determining the concentration of the analyte to thereby increase the accuracy of the analyte determination. Following this initially applied potential, the circuit is switched to an open circuit or to a potential that substantially reduces the current to minimize the rate of electrochemical potential at the working electrode. A second potential is applied between the electrodes and the current generated in the fluid test sample is measured to determine analyte concentration. Optionally, the accuracy of the analyte determination is further enhanced algorithmically.

SUMMARY OF THE INVENTION

Important aspects of the present invention are to provide a new and improved biosensor for determining the presence or amount of a substance in a sample including an oxidizable species as an internal reference and method of use of the biosensor.

In brief, a biosensor for determining the presence or amount of a substance in a sample and methods of use of the biosensor are provided. The biosensor for receiving a user sample to be analyzed includes a mixture for electrochemical reaction with an analyte. The mixture includes an enzyme, a mediator and an oxidizable species as an internal reference.

The internal reference is defined as the oxidizable species which in one embodiment can be further defined as the reduced form of a reversible redox couple that has an equal or higher redox potential than that of the mediator. The internal reference acts to increase the response current additively for operation potentials that oxidize both species and in the case where glucose is the analyte, a total response current is represented by:

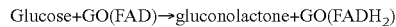

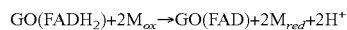

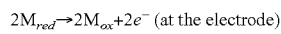

Where $I_{int-ref}$ is the portion of the total response current due to the internal reference, while $I_{glucose}$ is due to the oxidation of mediator proportional to the glucose concentration.

In accordance with features of the invention, the internal reference can be either the same mediator species or an oxidizable species with a higher redox potential than the mediator. Thus for biosensors with a low operation potential oxidizing only the mediator, the current lint-ref will be zero. However, for biosensors with a higher operation potential that oxidizes both species, the total response current will be the sum of the portion due to internal reference and that due to glucose. Since the internal reference concentration is fixed, the calibration slope of the sensor will only depend on the sensor response for glucose while the intercept will depend on the added amount of the internal reference. In another words, the internal reference will only offset the intercept and will not change the calibration slope. Thus, the concept of internal reference provides new and different ways to make glucose biosensors.

BRIEF DESCRIPTION OF THE DRAWINGS

The present invention together with the above and other objects and advantages may best be understood from the following detailed description of the preferred embodiments of the invention illustrated in the drawings, wherein.

DETAILED DESCRIPTION OF THE PREFERRED EMBODIMENTS

Figure 1A:
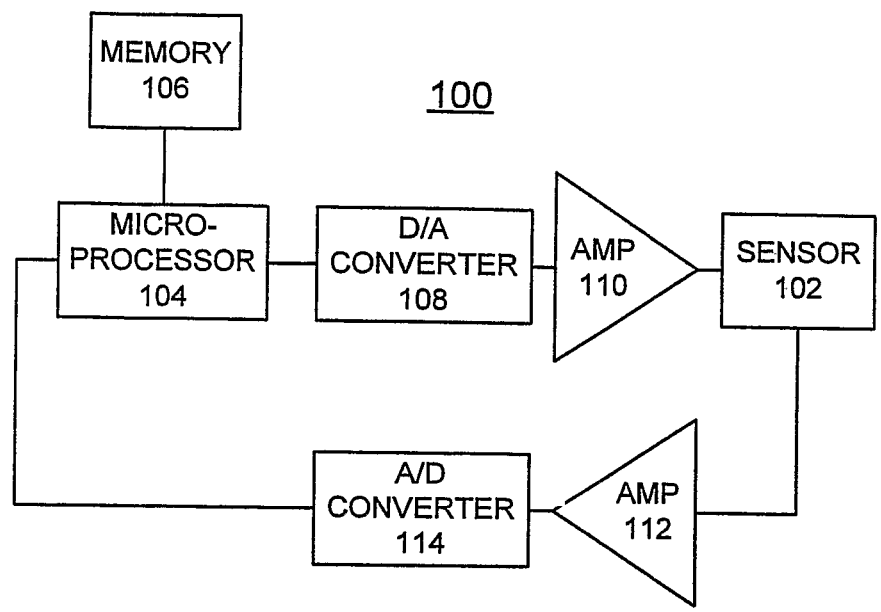
FIG. 1A is a block diagram representation of biosensor meter including a biosensor having an internal reference in accordance with the present invention.

The present invention relates to an electrochemical biosensor for determining the presence or amount of a substance in a sample. The biosensor includes sensor strips containing a working electrode and a counter electrode, each of which is at least partially covered with, for example, a separate reagent layer. The reagent layer on the working electrode includes, for example, an enzyme that interacts with an analyte through an oxidation-reduction reaction and also includes a mediator that is the oxidized form of a redox couple. The biosensor of the invention includes an internal reference or a reduced form of the mediator in the reagent layer on the working electrode. The internal reference is defined as an oxidizable species which in one embodiment can be further defined as a reduced form of a reversible redox couple that has an equal or higher redox potential than that of the mediator. A fixed quantative amount of the internal reference is provided in the reagent layer. The biosensors of the invention including the internal reference or added amount of the reduced form of mediator provide for improvements in that the internal reference acts to anchor the calibration intercept by nature of thermodynamics while maintaining the calibration slope.

Many compounds are useful as mediators due to their ability to accept electrons from the reduced enzyme and transfer them to the electrode. A necessary attribute of a mediator is the ability to remain in the oxidized state under the conditions present on the electrode surface prior to the use of the sensor. Among the more venerable mediators are the oxidized form of organometallic compounds, organic molecules, transition metal coordination complexes. A specific example of mediator is the potassium hexacyanoferrate (III), also known as ferricyanide.

As used in the following specification and claims, the term biosensor means an electrochemical sensor strip or sensor element of an analytical device or an instrument that responds selectively to analytes in an appropriate sample and converts their concentration into an electrical signal. The biosensor generates an electrical signal directly, facilitating a simple instrument design. Also, a biosensor offers the advantage of low material cost since a thin layer of chemicals is deposited on the electrodes and little material is wasted.

The term "sample" is defined as a composition containing an unknown amount of the analyte of interest. Typically, a sample for electrochemical analysis is in liquid form, and preferably the sample is an aqueous mixture. A sample may be a biological sample, such as blood, urine or saliva. A sample may be a derivative of a biological sample, such as an extract, a dilution, a filtrate, or a reconstituted precipitate.

The term "analyte" is defined as a substance in a sample, the presence or amount of which is to be determined. An analyte interacts with the oxidoreductase enzyme present during the analysis, and can be a substrate for the oxidoreductase, a coenzyme, or another substance that affects the interaction between the oxidoreductase and its substrate.

The term "oxidoreductase" is defined as any enzyme that facilitates the oxidation or reduction of a substrate. The term oxidoreductase includes "oxidases," which facilitate oxidation reactions in which molecular oxygen is the electron acceptor; "reductases," which facilitate reduction reactions in which the analyte is reduced and molecular oxygen is not the analyte; and "dehydrogenases," which facilitate oxidation reactions in which molecular oxygen is not the electron acceptor. See, for example, *Oxford Dictionary of Biochemistry and Molecular Biology, Revised Edition*, A. D. Smith, Ed., New York: Oxford University Press (1997) pp. 161, 476, 477, and 560.

The term "oxidation-reduction" reaction is defined as a chemical reaction between two species involving the transfer of at least one electron from one species to the other species. This type of reaction is also referred to as a "redox reaction." The oxidation portion of the reaction involves the loss of at least one electron by one of the species, and the reduction portion involves the addition of at least one electron to the other species. The ionic charge of a species that is oxidized is made more positive by an amount equal to the number of electrons transferred. Likewise, the ionic charge of a species that is reduced is made less positive by an amount equal to the number of electrons transferred.

The term "oxidation number" is defined as the formal ionic charge of a chemical species, such as an atom. A higher oxidation number, such as (III), is more positive, and a lower oxidation number, such as (II), is less positive. A neutral species has an ionic charge of zero. Oxidation of a species results in an increase in the oxidation number of that species, and reduction of a species results in a decrease in the oxidation number of that species.

The term "redox pair" is defined as two species of a chemical substance having different oxidation numbers. Reduction of the species having the higher oxidation number produces the species having the lower oxidation number. Alternatively, oxidation of the species having the lower oxidation number produces the species having the higher oxidation number.

The term "oxidizable species" is defined as the species of a redox pair having the lower oxidation number, and which is thus capable of being oxidized into the species having the higher oxidation number. Likewise, the term "reducible species" is defined as the species of a redox pair having the higher oxidation number, and which is thus capable of being reduced into the species having the lower oxidation number.

The term "organotransition metal complex," also referred to as "OTM complex," is defined as a complex where a transition metal is bonded to at least one carbon atom through a sigma bond (formal charge of −1 on the carbon atom sigma bonded to the transition metal) or a pi bond (formal charge of 0 on the carbon atoms pi bonded to the transition metal). For example, ferrocene is an OTM complex with two cyclopentadienyl (Cp) rings, each bonded through its five carbon atoms to an iron center by two pi bonds and one sigma bond. Another example of an OTM complex is ferricyanide (III) and its reduced ferrocyanide (II) counterpart, where six cyano ligands (formal charge of −1 on each of the 6 ligands) are sigma bonded to an iron center through the carbon atoms of the cyano groups.

The term "coordination complex" is defined as a complex having well-defined coordination geometry, such as octahedral or square planar geometry. Unlike OTM complexes, which are defined by their bonding, coordination complexes are defined by their geometry. Thus, coordination complexes may be OTM complexes (such as the previously mentioned ferricyanide), or complexes where non-metal atoms other than carbon, such as heteroatoms including nitrogen, sulfur, oxygen, and phosphorous, are datively bonded to the transition metal center. For example, ruthenium hexaamine, or hexaminoruthenate (II)/(III), is a coordination complex having a well-defined octahedral geometry where six $NH_3$ ligands (formal charge of 0 on each of the 6 ligands) are datively bonded to the ruthenium center. Ferricyanide is also an example of the coordination complex that has the octahedral geometry. A more complete discussion of organotransition metal complexes, coordination complexes, and transition metal bonding may be found in Collman et al., *Principles and Applications of Organotransition Metal Chemistry* (1987) and Miessler & Tarr, *Inorganic Chemistry* (1991).

The term "mediator" is defined as a substance that can be oxidized or reduced and that can transfer one or more electrons between a first substance and a second substance. A mediator is a reagent in an electrochemical analysis and is not the analyte of interest. In a simplistic system, the mediator undergoes a redox reaction with the oxidoreductase after the oxidoreductase has been reduced or oxidized through its contact with an appropriate substrate. This oxidized or reduced mediator then undergoes the opposite reaction at the electrode and is regenerated to its original oxidation number.

The term "electroactive organic molecule" is defined as an organic molecule that does not contain a metal and that is capable of undergoing an oxidation or reduction reaction. Electroactive organic molecules can behave as redox species and as mediators. Examples of electroactive organic molecules include coenzyme pyrroloquinoline quinone (PQQ), benzoquinones and naphthoquinones, N-oxides, nitroso compounds, hydroxylamines, oxines, flavins, phenazines, phenothiazines, indophenols, and indamines.

The term "electrode" is defined as an electrically conductive substance that remains stationary during an electrochemical analysis. Examples of electrode materials include solid metals; metal pastes, conductive carbon, conductive carbon pastes, and conductive polymers.

Having reference now to the drawings, in FIG. 1 there is illustrated a biosensor meter designated as a whole by the reference character 100 of the preferred embodiment and arranged in accordance with principles of the present invention. Biosensor meter 100 includes a biosensor 102 arranged in accordance with principles of the present invention. Biosensor meter 100 includes microprocessor 104 together with an associated memory 106 for storing program and user data. Digital data from the microprocessor 104 is applied to a digital-to-analog (D/A) converter 108. D/A converter 108 converts the digital data to an analog signal. An amplifier 110 coupled to the D/A converter 108 amplifies the analog signal. The amplified analog signal output of amplifier 110 is applied to the biosensor 102 of the invention. Biosensor 102 is coupled to an amplifier 112. The amplified sensed signal is applied to an analog-to-digital (A/D) converter 114 that converts the amplified, analog sensor signal to a digital signal. The digital signal is applied to the microprocessor 104.

Most of the commercially available disposable biosensors used for monitoring blood glucose require the deposition/printing of a mixture of an enzyme and a mediator with some binding agent. For the application of glucose measurement, the mediator is in the oxidized form of a redox couple. Depending on the redox couple, the mediator can be a very strong oxidant, such as ferricyanide, thereby chemically oxidizing the functional groups after mixing with the enzyme and the binding agent. Subsequently, a small amount of the reduced mediator is formed as impurity in the reagent in the processes of ink mixing, storage and printing. Thus, the end result of mixing and printing the reagent ink is the generation of the reduced form of the redox couple, giving rise to the background current. The formation of this reduced form of the mediator and thus the background current may vary from batch to batch. This process-generated reduced form of the mediator, such as ferrocyanide from ferricyanide, can be oxidized in general to minimize the background signal using the algorithm outlined in the U.S. Pat. Nos. 5,620,579 and 5,653,863, to Genshaw et al., and assigned to the present assignee. However, the process-dependent background signal, which is translated into the calibration intercept, can be spread out in a range of values. At the extremes of these diverged values of intercept, analytical accuracy will be suffered because no reasonable calibration intercept can be assigned to accommodate the diverged intercept.

In accordance with features of the invention, a grade of mediator that contains a certain level of the reduced form of the mediator in the reagent is used for decreasing the effect of the strong oxidant. Thermodynamically, the presence of a small amount of the reduced form of the mediator in the ink mixture of enzyme and mediator decreases the driving force for the conversion from the oxidized to the reduced form. This is advantageously accomplished by adding a small fixed amount of the reduced form of the mediator to the oxidized mediator.

Even though background signal will be generated, the algorithm in the U.S. Pat. Nos. 5,620,579 and 5,653,863 will minimize the effect of background to increase the accuracy of the glucose sensor. The above-identified patents disclose a method that reduces the background bias due to oxidizable impurities in an amperometric sensor used for measuring a specific analyte, such as glucose, in blood. The background current of such a sensor will increase if it is stored over a long period of time or under stress (heat, moisture, etc.) due to the increased presence of reduced mediator or other reduced impurity present in the sensor such as enzyme stabilizers, e.g. glutamate, and surfactants having reducing equivalents. For example, in a ferricyanide based amperometric sensor, the background bias is related to the presence of ferrocyanide (from the reduction of ferricyanide) near the electrode surface. This accumulated ferrocyanide, as opposed to the ferrocyanide produced during use of the sensor (fresh ferrocyanide), is oxidized back to ferricyanide to reduce the background bias it causes and thereby extend the sensor shelf life. To achieve this objective, the method uses an electrochemical approach. The background bias is further reduced when the electrochemical approach is augmented with an algorithmic correction.

The disclosed method involves first applying a positive potential pulse (called the "burn-off" pulse) which precedes the normal potential profile during use of the biosensor. This is typically accomplished by applying a positive potential of from 0.1 to 0.9 volt (preferably 0.3 to 0.7 volt) between the working and reference electrodes of the sensor for a period of from 1 to 15 seconds (preferably 5 to 10 seconds). The burn-off pulse oxidizes the initial ferrocyanide (or other oxidizable impurity), so that the sensor can begin the assay with a clean background. Typically, the background is not perfectly clean since only a portion of the oxidizable impurity is oxidized by the burn-off pulse. This is the case because the chemical layer covers both the working and the counter electrodes. The initial ferrocyanide exists in the chemical layer since it comes from ferricyanide. When sample fluid is applied and the chemical layer re-hydrates, the ferrocyanide near the working electrode is re-oxidized. The rest of the ferrocyanide diffuses into the sample fluid and is mixed with the glucose. That portion of the initial ferrocyanide cannot be re-oxidized without affecting the glucose. The initial ferrocyanide is near the electrode for a very short time (a few seconds) after the fluid test sample is applied. The reason for this is that the chemicals (enzyme and ferricyanide, etc.) are deposited as a thin layer on the working and counter electrodes. The burn-off technique takes advantage of this since a significant amount of the initial ferrocyanide can be burned off without noticeable reduction of the analyte concentration in the fluid test sample most of which does not come into direct contact with the electrode. Experiments have demonstrated that the background bias of a stressed sensor can be reduced by 40% with proper application of the burn-off pulse.

The disclosed method of the U.S. Pat. Nos. 5,620,579 and 5,653,863 advantageously is applied to minimize the effect of background signal to increase the accuracy of the glucose biosensor meter 100 of the preferred embodiment. The subject matter of the above-identified patents is incorporated herein by reference.

In accordance with features of the invention, the added amount of the reduced form of mediator acts to anchor the calibration intercept by nature of thermodynamics while maintaining the calibration slope. In light of the function the reduced form of mediator, for example, ferrocyanide, plays in the glucose sensor, it is referred to as the internal reference.

Examples of electroactive organic molecule mediators are described in U.S. Pat. No. 5,520,786, issued to Bloczynski et al. on May 28, 1996, and assigned to the present assignee. In particular, a disclosed mediator (compound 18 in TABLE 1) comprising 3-phenylimino-3H-phenothiazine referred to herein as MLB-92, has been used to make a glucose biosensor 102 in accordance with features of the invention. The subject matter of the above-identified patent is incorporated herein by reference.

A commercially available biosensor meter and biosensor is manufactured and sold by Bayer Corporation under the trademark Ascensia DEX. The Ascensia DEX biosensor includes generally as pure a form of ferricyanide as possible for the reagent. The Ascensia DEX biosensor has been used to make a glucose biosensor 102 in accordance with features of the invention by adding an adequate amount of ferrocyanide to the pure ferricyanide. Benefits of adding ferrocyanide defining the internal reference of biosensor 102 to the Ascensia DEX reagent ink include an immediate benefit of increasing the intercept without changing slope, anchoring the intercept range, and increasing long-term stability of biosensor during storage.

In accordance with features of the invention, the MLB-92 mediator having a lower redox potential was used to make a glucose biosensor 102 with special properties. With the addition of adequate amounts of the internal reference, ferrocyanide, the new biosensor system can be made to work with two operation potentials: (1) at 400 mV where both the new mediator and the internal reference are oxidized, and (2) at 100 mV where only the new mediator can be oxidized. The significance of this approach is two-fold. First, the glucose biosensor 102 such formulated (new mediator and internal reference) can be operated at a high potential (+400 mV) to produce currents in a range that fits the calibration characteristics of the hardware requirements of the existing instrument. Secondly, since the lower redox potential and thus a lower oxidation power of the mediator will likely to have virtually no conversion of the oxidized form to the reduced form of the mediator, a lower operation potential (0-100 mV) can be applied to the sensor so as to avoid the oxidation of the internal reference. Thus, a new set of calibration characteristics based on the new mediator, most likely with near zero intercept due to the lower oxidation power, will lead to a better analytical precision for glucose measurements. It will also reduce the matrix interference in the whole blood by avoiding the oxidation of some of the known oxidizable species such as uric acid and acetaminophen.

In accordance with features of the invention, another application of the internal reference to glucose sensors 102 is to add adequately large amount of internal reference to the biosensor system to produce a high current response. Using the double steps algorithm with open circuit between them (Bayer U.S. Pat. No. 5,620,579 and No. 5,653,863), the first potential step is set at 400 mV to produce a current that is mostly due to the internal reference signal while the second step is set at a low potential (0-100 mV) to produce a current signal related to the glucose concentration only. The ratio of the first signal, which should be virtually independent of the whole blood hematocrit, to the second signal at low potential can be used to correct for the analytical bias due to hematocrit effect.

In accordance with features of the invention, the internal reference is defined as the oxidizable species which in one embodiment is further defined as the reduced form of a reversible redox couple that has an equal or higher redox potential than that of the mediator. The concept and use of an internal reference are very common in the field of analytical chemistry. However, no example of using an internal reference for biosensors has been suggested in existing patents or literature. In all three scenarios described above, the internal reference acts to increase the response current additively for operation potentials that oxidize both species and with glucose as the analyte; a total response current is represented by:

$$I_{total} = I_{int-ref} + I_{glucose}$$

$$I_{int-ref} \propto \text{(internal reference) and } I_{glucose} \propto \text{(glucose)};$$

Where $I_{int-ref}$ is the portion of the total response current due to the internal reference, while $I_{glucose}$ is due to the oxidation of mediator proportional to the glucose concentration.

In accordance with features of the invention, the internal reference can be either the same mediator species or an oxidizable species with a higher redox potential than the mediator. Thus for biosensors with a low operation potential oxidizing only the mediator, the current $I_{int-ref}$ will be zero. However, for biosensors with a higher operation potential that oxidizes both species, the total response current will be the sum of the portion due to internal reference and that due to glucose. Since the internal reference concentration is fixed, the calibration slope of the sensor will only depend on the sensor response for glucose while the intercept will depend on the added amount of the internal reference. In another words, the internal reference will only offset the intercept and will not change the calibration slope. Thus, the concept of internal reference provides new and different ways to make glucose biosensors.

Figures 1B, 1C, 1D:
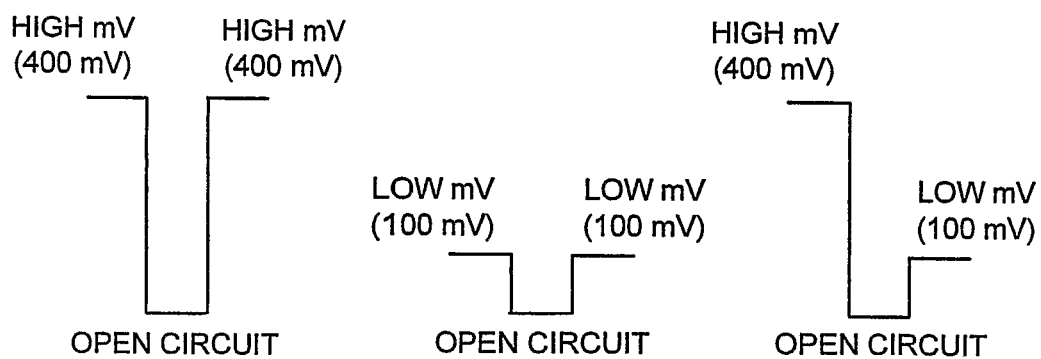
FIGS. 1B, 1C, and 1D are diagrams respectively illustrating operational methods for use with the biosensor of FIG. 1 of the invention.

Referring now to FIGS. 1B, 1C, and 1D, there are at least three modes of operation based on the use of internal reference for glucose biosensors 102 of the invention. Potentiostatically, the three of modes of operation are represented in FIGS. 1B, 1C, and 1D. Each of the illustrated modes of operation include a first burnoff pulse, followed by a second wait period or open circuit, and a final third read pulse, each pulse or period having a selected duration, for example, 10 seconds. In the basic and most immediate operation, ferrocyanide is retained in ferricyanide at the concentration of 0.1 to 1% of the total ferricyanide providing the internal reference for glucose biosensors 102 of the invention. This is depicted in FIG. 1B where both potentials in the first and the third periods are at the same voltage, for example 400 mV. Retaining of a small percentage of ferrocyanide defining the internal reference can be accomplished either by an appropriate purification process of ferricyanide or by adding an adequate amount of ferrocyanide to the pure ferricyanide. The outcome of these retaining processes is to keep deliberately a desirable amount of ferrocyanide in ferricyanide as a special grade of ferricyanide. This is in contrast to the conventional wisdom of having as pure a form of ferricyanide as possible, such as for the DEX reagent, usually ferrocyanide in the order of 0.05% of ferricyanide or less as impurity. The most desirable amount is 0.1% ferrocyanide in the final formulation for DEX sensor, which will lead to the anchoring of the calibration intercept at a narrower range while maintaining the calibration slope for the DEX sensor.

In FIG. 1C the second mode of operation is shown, where a desirable amount of ferrocyanide (the internal reference) is added to the reagent of enzyme and a mediator with a redox potential lower than that of the internal reference. The biosensor 102 is expected to work under high and low potentials (for example at 400 mV and 100 mV vs. Ag/AgCl) for existing instruments and instruments with a new hardware requirement. This biosensor can be operated in potential programs depicted in FIG. 1B for existing instruments 100 and FIG. 1C for new instruments 100. Examples of the mediator and internal reference combination include the system of MLB-92 and ferrocyanide as well as ruthenium hexaamine and ferrocyanide. The separation of the two redox potentials is large enough so that there will be generally no oxidation of the internal reference species when operated at the low voltage.

In FIG. 1D the third mode of operation is shown, where a higher but desirable concentration of ferrocyanide is added to the reagent mixture of enzyme and a mediator with a redox potential lower than that of the internal reference. The amount of the internal reference would produce a current equivalent to about 50% to 75% of the full scale in the calibration range preferably. In the operation algorithm, the first potential step is set to oxidize both the mediator and the internal reference (400 mV) while the second potential step for the read pulse is to oxidize the mediator only (0-100 mV). The current in the first potential step of FIG. 1D will be most pertinent to the internal reference that is immediately next to the electrode and should have virtually no hematocrit effect. The ratio of the current from the second step to that from the first step will provide a correction for the analytical bias due to hematocrit effect.

Experiments have been carried out to show the feasibility of the method of adding internal reference to a mediator system to overcome existing problems or to enhance sensor performance in accordance with the biosensor 102 of the invention.

Figure 2A:
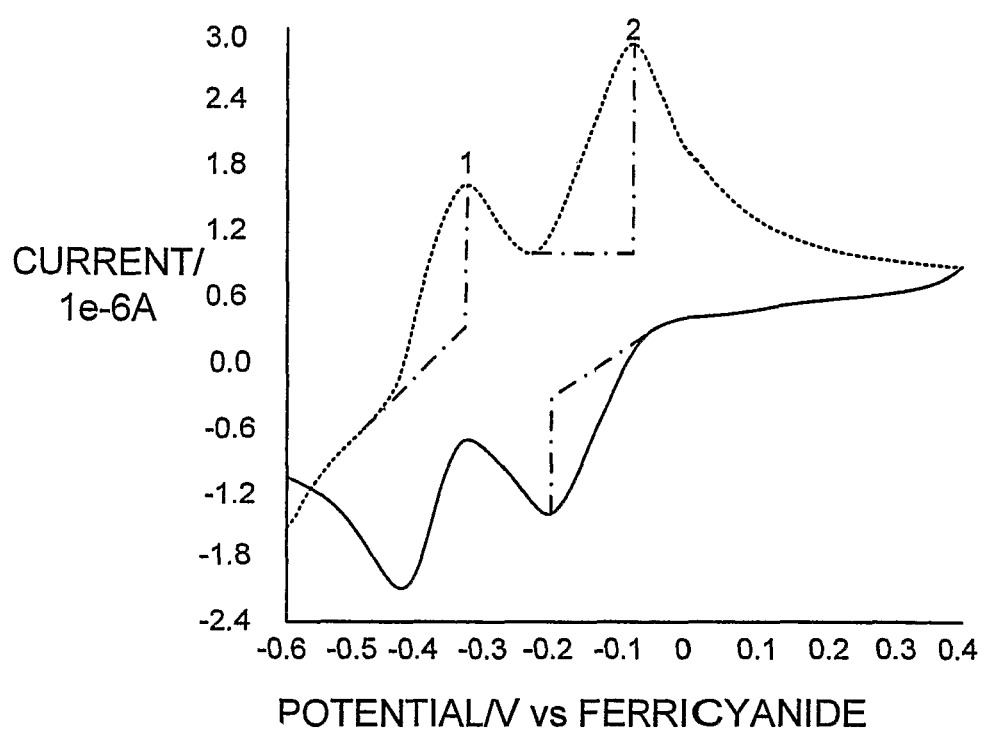
FIGS. 2A, 2B, and 2C are charts showing three cyclic voltammograms of MLB based glucose biosensors with ferrocyanide as the internal reference the biosensor of FIG. 1 of the invention in whole blood samples of 0 mg/dL glucose.
Figure 2B:
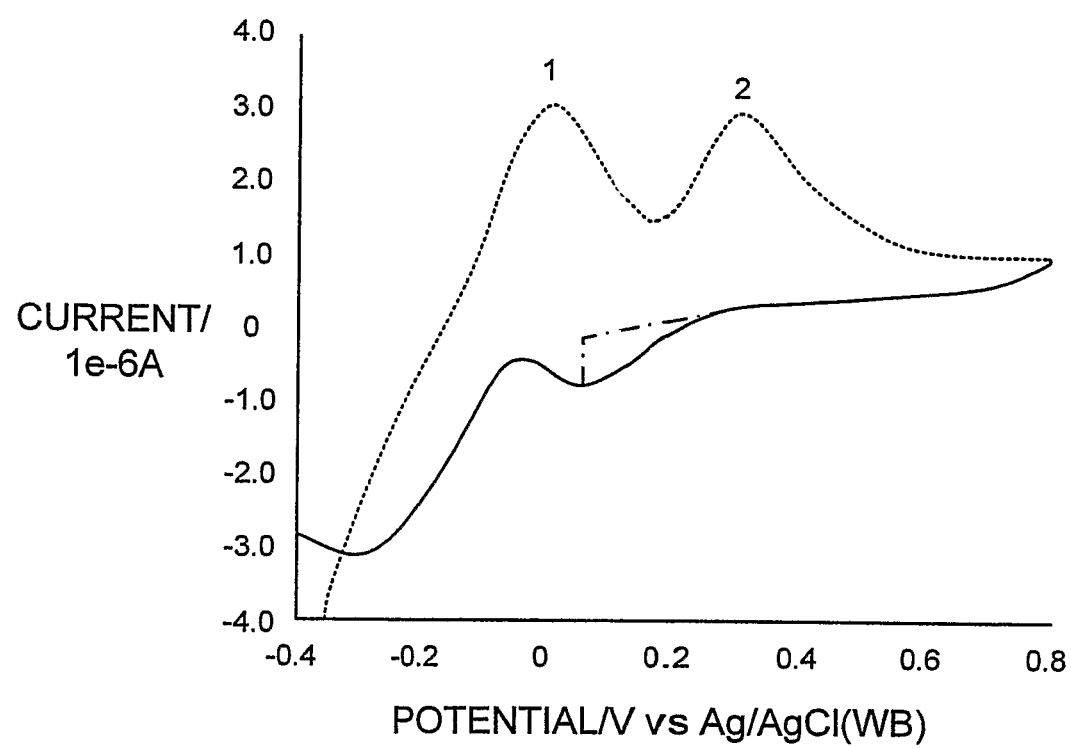
Figure 2C:
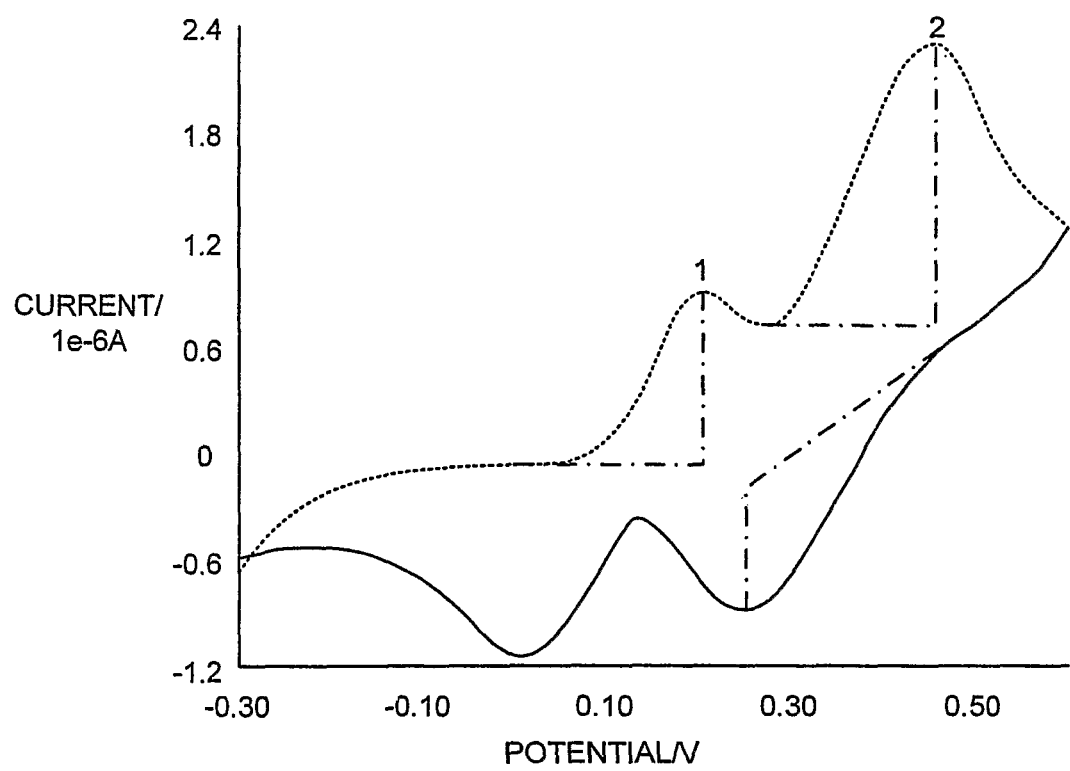

Referring now to FIGS. 2A, 2B, and 2C, there are shown three cyclic voltammograms illustrating operation of the biosensor 102 of the invention. The illustrated three cyclic voltammograms are for MLB based glucose biosensors 102 with ferrocyanide as the internal reference in whole blood samples of 0 mg/dL glucose.

FIG. 2A illustrates working electrode vs. ferricyanide counter electrode, FIG. 2B illustrates working electrode vs. silver (Ag) and silver chloride (AgCl) or Ag/AgCl counter electrode and FIG. 2C illustrates working electrode vs. MLB-92 counter electrode. Respective peaks labeled 1 and 2 represent the oxidation of the mediator $MLB_{red}$ (reduced form of MLB) and the internal reference ferrocyanide respectively for all three voltammogram plots. The oxidation peak for $MLB_{red}$ shifts along the potential scale as the redox couple on the counter electrode changes from ferricyanide to Ag/AgCl to MLB-92. However, it can be seen that the relative position of the mediator MLB-92 to the internal reference ferrocyanide is the same in all three voltammogram plots of FIGS. 2A, 2B, and 2C.

Figure 3:
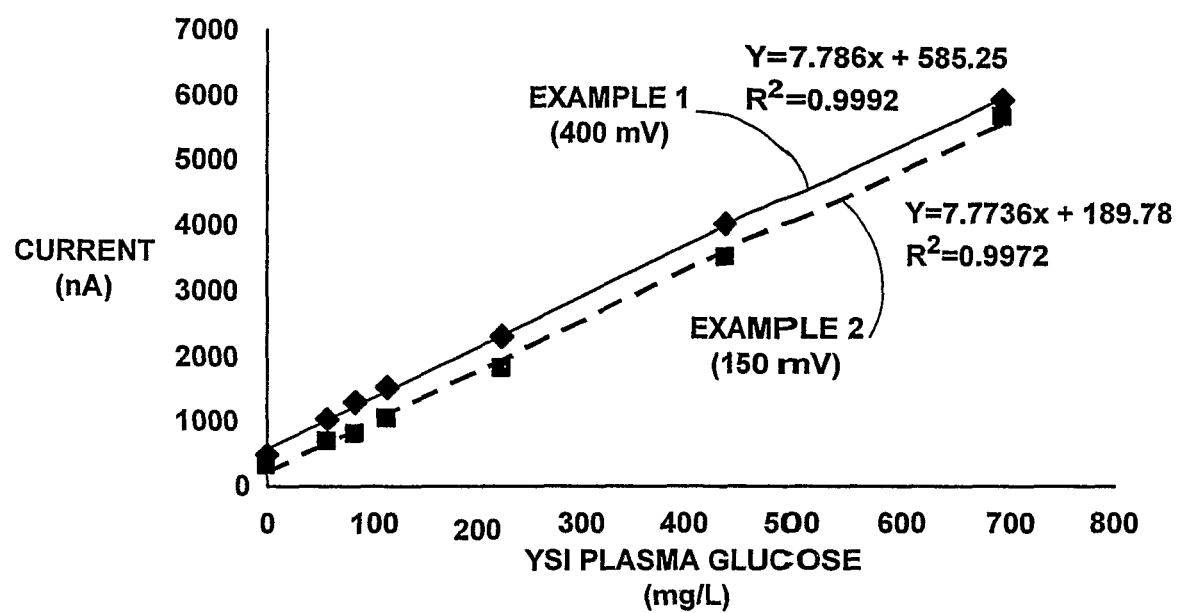
FIG. 3 is a chart illustrating a linear response of the biosensor of FIG. 1 of the invention at different voltage operating potentials.

Referring to FIG. 3, there shown in FIG. 3 is a chart illustrating a linear response of the biosensor 102 of the invention at different voltage operating potentials. The biosensor 102 is operated at (1) 400 mV potential and (2) 150 mV potential. FIG. 3 illustrates the linear dose response of MLB-92 mediator based biosensor 102 with 20 mM ferrocyanide as the internal reference. Respective lines labeled EXAMPLE 1 and EXAMPLE 2 are from 400 mV and 150 mV operation potentials against Ag/AgCl counter electrode. As shown in FIG. 3, the biosensor 102 gives virtually the same slope but with different intercepts for operations at 400 mV and 150 mV potentials. This result demonstrates that the internal reference can be selectively oxidized or avoided by the operation potential. Thus, one biosensor 102 can serve for two different meters.

Examples of the biosensor 102 have been prepared systematically showing the increase of intercept with increasing ferrocyanide as the internal reference while the slopes were kept virtually unchanged. Three working electrode reagents were prepared in the following formulations. These three reagents were pin-deposited on to two sensor formats: (1) Ag/AgCl as the counter electrode, (2) 10% printed ferricyanide as the counter electrode.

| Formulations | Enzyme, PQQ-GDH | Mediator MLB-92 | Internal Reference Ferricyanide | Buffer and binding agent, |
|---|---|---|---|---|
| 1 | 20 unit/μL | 24 mM | 0 mM | 0.1 M NaCl + phosphate, 1% CMC |
| 2 | 20 unit/μL | 24 mM | 4 mM | 0.1 M NaCl + phosphate, 1% CMC |
| 3 | 20 unit/μL | 24 mM | 8 mM | 0.1 M NaCl + phosphate, 1% CMC |

Figure 4:
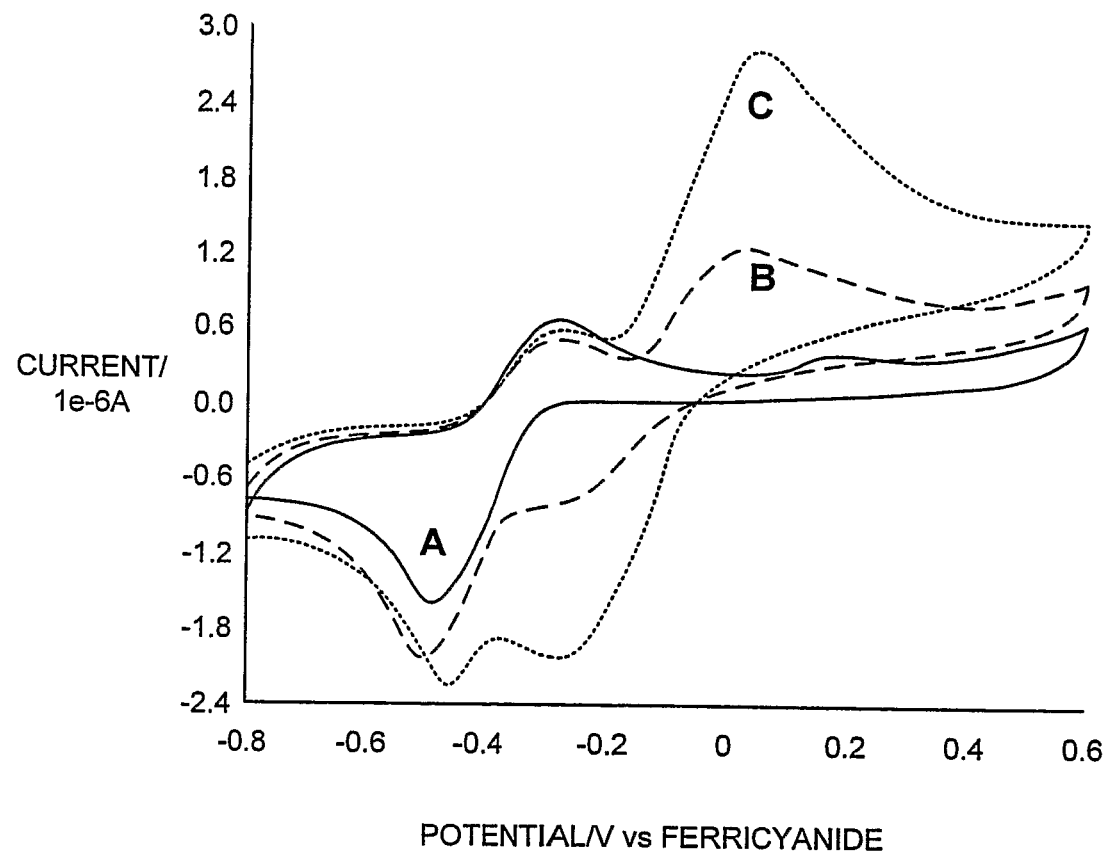
FIG. 4 is a chart illustrating effect of the added internal reference to the overall voltammetric current using biosensors of FIG. 1 of the invention with 10% printed ferricyanide as the counter electrode.

FIG. 4 illustrates effect of the added internal reference to the overall voltammetric current using biosensors 102 of the invention with 10% printed ferricyanide as the counter electrode. FIG. 4 provides cyclic voltammograms of sensors with ferrocyanide as the internal reference in whole blood samples of 0 mg/L glucose. Voltammograms labeled A, B and C are with formulations 1, 2 and 3 respectively all with a counter electrode of 10% printed ferricyanide.

The effect of the added internal reference to the overall voltammetric current is shown in FIG. 4 using sensors with 10% printed ferricyanide as the counter electrode. The main oxidation/reduction peaks here are centered around −0.38 Volt vs. 10% ferricyanide, which is due to the mediator MLB. The oxidation peak at about 0-50 mV is due to the internal reference of ferrocyanide. While the oxidation peak for the internal reference ferrocyanide increases with the increases of the internal reference concentration from 0 to 4 to 8 mM, the oxidation peak for the mediator is virtually unchanged. Here the concept of internal reference is explained further by the fact that the main oxidation peak of $MLB_{red}$ is unaffected by the presence of the internal reference.

Figure 5A:
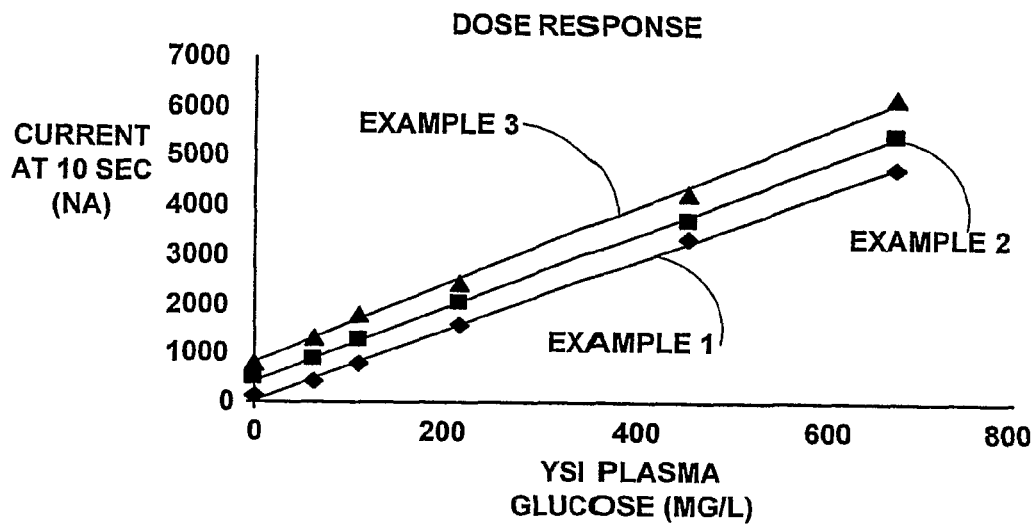
FIGS. 5A and 5B are charts illustrating linear response and increased intercept with increasing internal reference of MLB based biosensors of FIG. 1 of the invention with Ag/AgCl as the counter electrode.
Figure 5B:
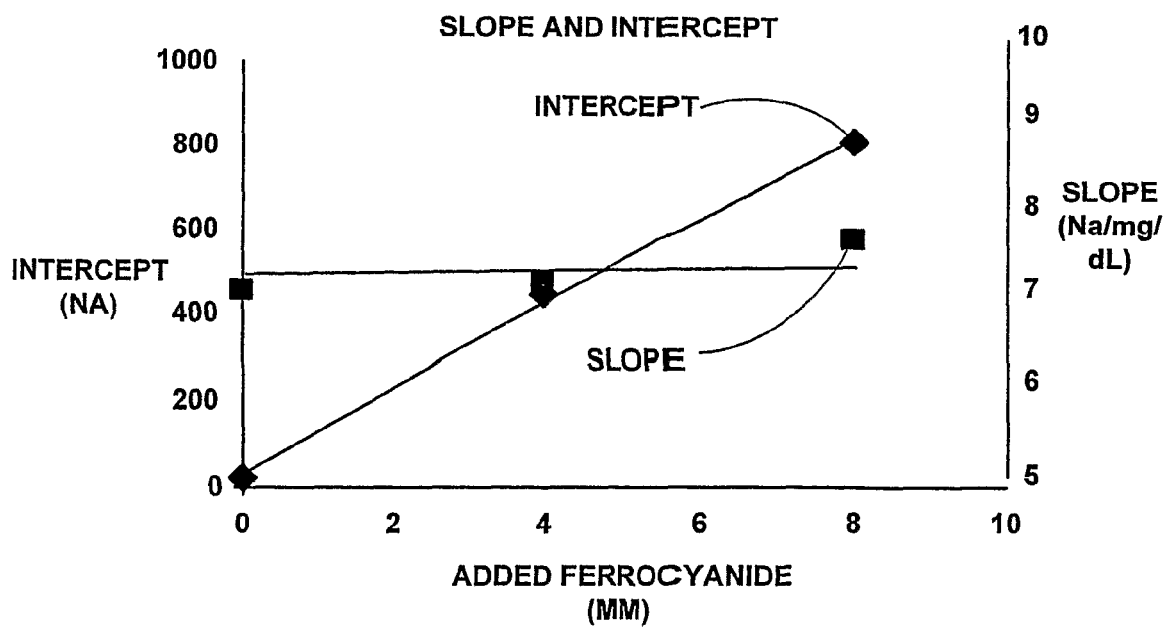

Referring to FIGS. 5A and 5B, charts illustrating linear response and increased intercept with increasing internal reference of MLB based biosensors 102 of the invention with Ag/AgCl as the counter electrode are shown. FIG. 5A illustrates the linear dose response of MLB based biosensors 102 with 0, 4, and 8 mM ferrocyanide, respectively labeled EXAMPLE 1, EXAMPLE 2, and EXAMPLE 3. FIG. 5B illustrates intercept and slope as a function of added ferrocyanide in the working electrode reagent of the biosensor 102 of the invention. All three sensors used Ag/AgCl as the counter electrode.

Figure 6A:
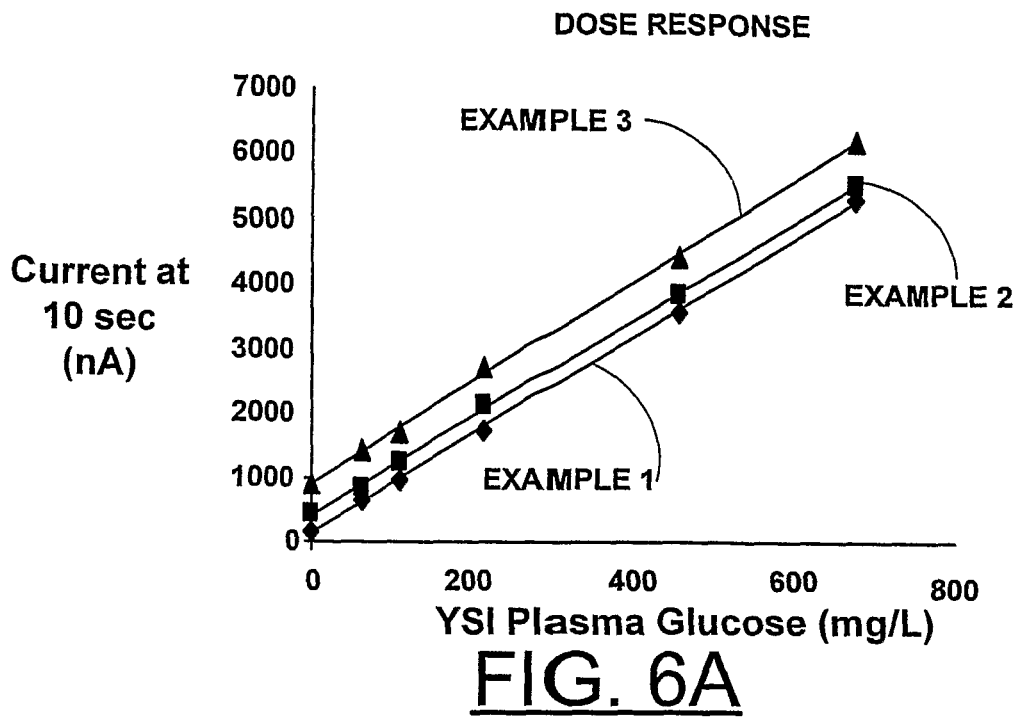
FIGS. 6A and 6B are charts illustrating linear response and increased intercept with increasing internal reference of MLB based biosensors of FIG. 1 of the invention with 10% ferricyanide as the counter electrode.
Figure 6B:
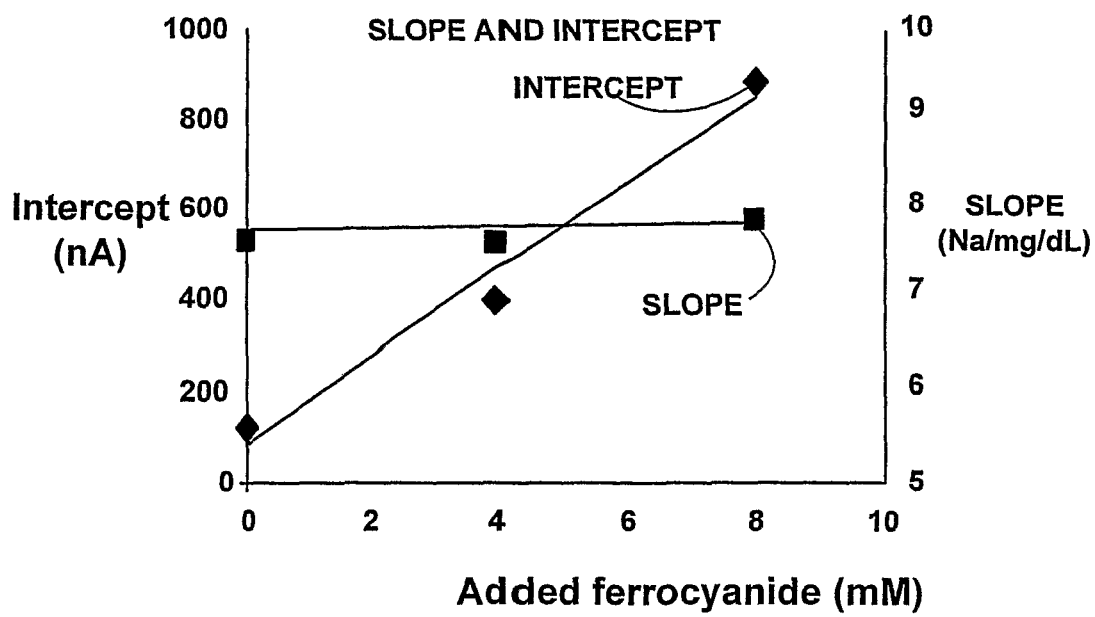

Referring also to FIGS. 6A and 6B, charts illustrating linear response and increased intercept with increasing internal reference of MLB based biosensors 102 of the invention with 10% ferricyanide as the counter electrode are shown. FIG. 6A illustrates the linear dose response of MLB based biosensors 102 with 0, 4, and 8 mM ferrocyanide, respectively labeled EXAMPLE 1, EXAMPLE 2, and EXAMPLE 3. FIG. 6B illustrates intercept and slope as a function of added ferrocyanide in the working electrode reagent of the biosensor 102 of the invention. All three sensors used 10% printed ferricyanide as the counter electrode.

In the dose response experiments, both sensor series with Ag/AgCl counter electrode of FIGS. 5A and 5B, and 10% ferricyanide counter electrode of FIGS. 6A and 6B show linear response and increased intercept with increasing internal reference. For practical purpose, the slope of the three sensors in FIGS. 5A and 5B is unchanged while the intercept increases linearly with the added ferrocyanide. The same linear relationship of intercept with added ferrocyanide and the flat slope trend are repeated in sensor series with the % printed ferricyanide as the counter electrode, as shown in FIGS. 6A and 6B.

Experiments have been carried out to show the addition of ferrocyanide to DEX reagent ink, modification of calibration intercept without changing slope in accordance with the biosensor 102 of the invention.

Figure 7:
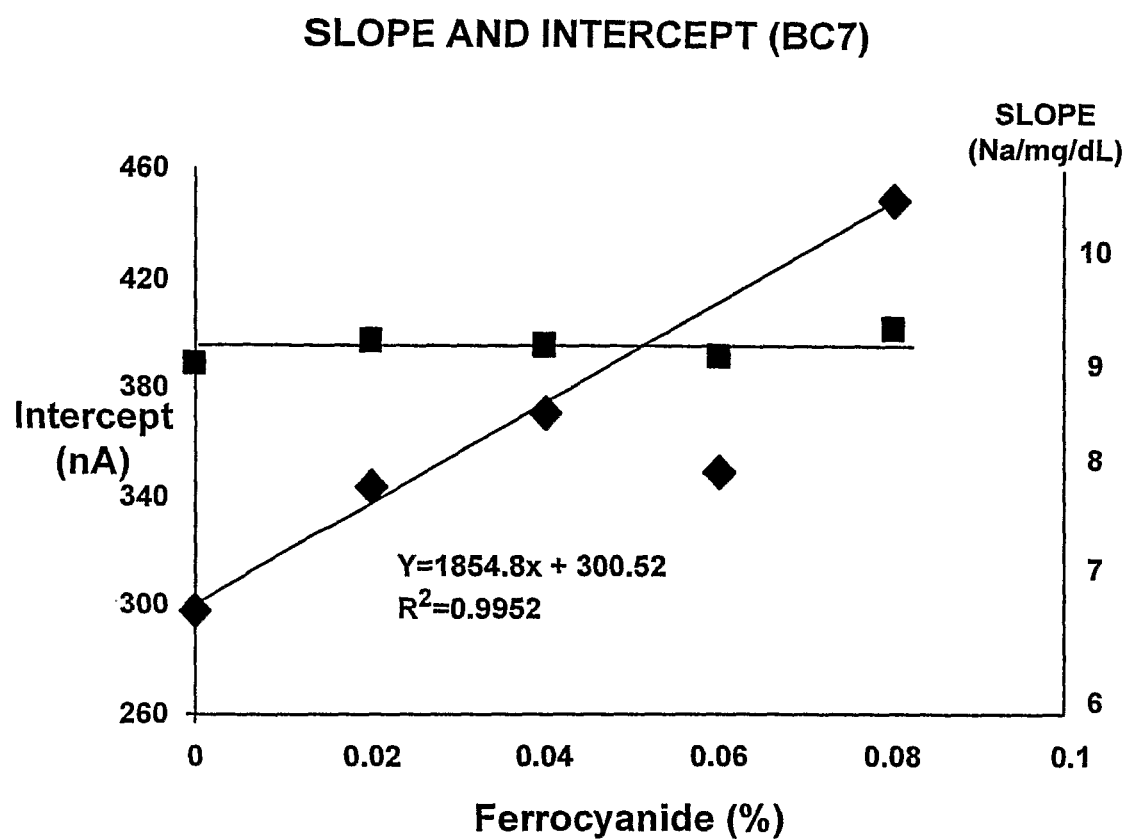
FIG. 7 is a chart illustrating linear relationship of the calibration intercept with increasing internal reference of DEX biosensors of FIG. 1 of the invention with 10% ferricyanide as the counter electrode.

FIG. 7 illustrates linear relationship of the calibration intercept with increasing internal reference of DEX type biosensors 102 of the invention. Five different formulations in a set format labeled BC7 in FIG. 7 were made with 0, 0.02, 0.04, 0.06 and 0.08% ferrocyanide mixed in the standard DEX reagent for the DEX sensor. The regression slope and intercepts for these five sensors of the BC7 format are shown in FIG. 7. Except for sensor with 0.06% ferrocyanide due to the experimental problems, the intercepts of the other four sensors give a nice linear function with respect to the added amount of ferrocyanide as the internal reference. On the other hand, the slopes of all five sensors fall in a flat line indicating that the addition of the internal reference does not change the slope of the DEX type biosensors 102 of the invention.

Figure 8A:
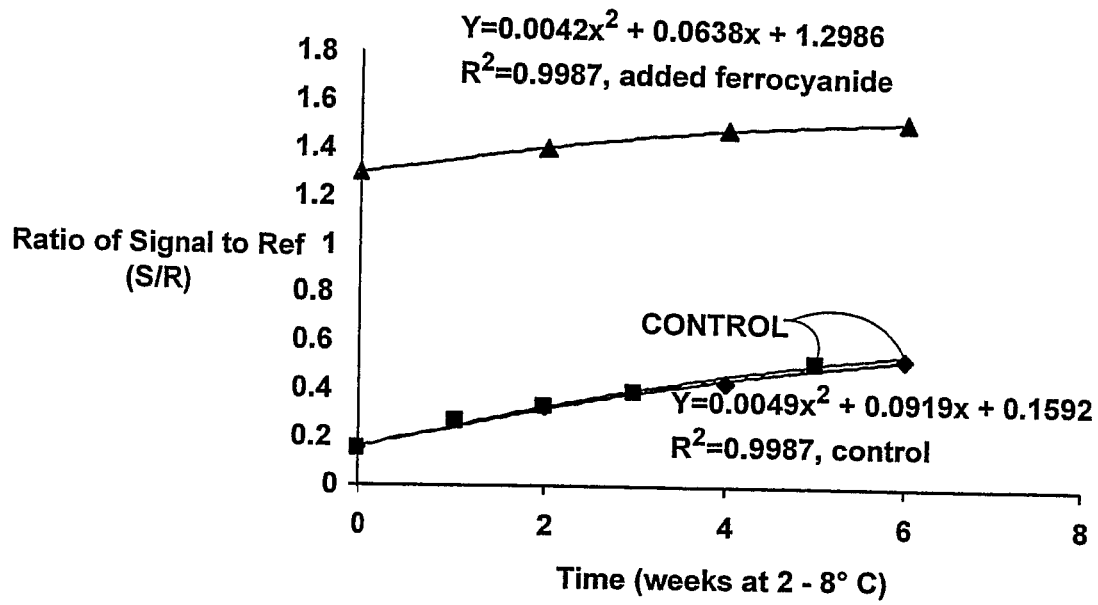
FIGS. 8A and 8B are charts illustrating the ratio of signal to reference results from flow-injection-analysis (FIA) of the residual ferrocyanide from a control reagent ink and the reagent ink with 0.1% ferrocyanide added to the reagent mixture of 20% ferricyanide of a biosensor of FIG. 1 of the invention.
Figure 8B:
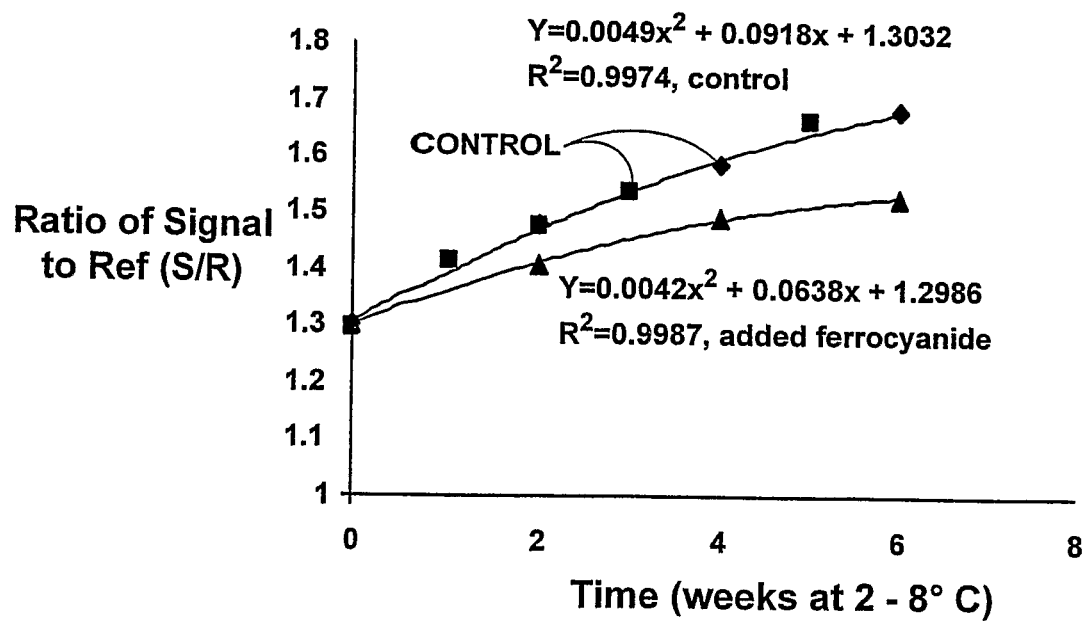

FIGS. 8A and 8B illustrate the ratio of signal to reference results from flow-injection-analysis (FIA) of the residual ferrocyanide from a control reagent ink and the reagent ink with 0.1% ferrocyanide added to the reagent mixture of 20% ferricyanide of a biosensor 102 of the invention. One of the subtle effects of adding the internal reference ferrocyanide to the DEX reagent ink is to decrease the driving force for the conversion of the mediator ferricyanide to ferrocyanide. Thus, ferricyanide becomes the source of the residual current in the DEX sensor. One way of showing this subtle effect is to monitor the increase of the residual current (background current) of the reagent ink with internal reference along with the control reagent ink over a long period of time. Both reagent inks were stored in refrigeration (2-8° C.) over several weeks. FIG. 8 shows the results of FIA of the residual ferrocyanide from both reagent inks. From FIG. 8, the ratio of signal-to-reference (S/R) represents the relative amount of ferrocyanide from the reagent ink compared to the added ferrocyanide as the reference in FIA. Thus, the higher the value of S/R from the FIA analysis, the higher the ferrocyanide in the reagent inks. It can be seen from FIG. 8A that the S/R value increase over the period of six weeks for both the control inks and the reagent ink with added ferrocyanide. However, the reagent ink curve with added ferrocyanide has a slower increase of residual current over the period of six weeks compared to control curves. In FIG. 8B, the S/R response curves from the control inks and the reagent ink with added ferrocyanide are merged together for comparison. To the first order approximation (since the coefficients for the second order terms of both second order polynomials are very small), the rate of residual current increase over six weeks during refrigeration is about 30% ([0.0918−0.0638]/0.0918=30%) smaller for the reagent ink curve with added ferrocyanide than for the control curves. Thus, it may be understood from FIGS. 8A and 8B that the rate of the ferricyanide-to-ferrocyanide conversion in reagent ink is decreased substantially by the addition of the internal reference ferrocyanide to the DEX reagent ink in accordance with biosensor 102 of the invention.

While the present invention has been described with reference to the details of the embodiments of the invention shown in the drawings, these details are not intended to limit the scope of the invention as claimed in the appended claims.

What is claimed is:

1. A biosensor for determination of an analyte concentration in a test sample comprising:
   a working electrode and a counter electrode;

a mixture for electrochemical reaction with an analyte, said mixture including an enzyme, a mediator, and an oxidizable species as an internal reference, the oxidizable species being different than the mediator species and having different redox potentials, said mixture being located as a single layer directly on a surface of at least a portion of the working electrode and the counter electrode prior to the introduction of the test sample, wherein the mixture includes only one enzyme.

2. The biosensor of claim 1 wherein said internal reference is a reduced form of a reversible redox couple that has a higher redox potential than that of said mediator.

3. The biosensor of claim 1 wherein said mediator comprises 3-phenylimino-3H-phenothiazine.

4. The biosensor of claim 3 wherein said internal reference comprises ferrocyanide.

5. The biosensor of claim 4 wherein said ferrocyanide and said mediator are oxidized at a first voltage potential and only said mediator is oxidized at a second voltage potential, said second voltage potential being less than said first voltage potential.

6. The biosensor of claim 5 wherein said first voltage potential is about 400 mV and said second voltage potential is about 100 mV.

7. The biosensor of claim 1 wherein said mediator comprises ruthenium hexamine.

8. The biosensor of claim 7 wherein said internal reference comprises ferrocyanide.

9. The biosensor of claim 8 wherein said enzyme comprises glucose oxidase.

10. A method of forming and applying a reagent mixture for an electrochemical reaction with an analyte of a fluid sample in a biosensor, the biosensor having a working electrode and a counter electrode, the method comprising:
    forming a batch of reagent mixture by adding an enzyme, adding a mediator and adding a known amount of an oxidizable species, the added oxidizable species being added separately from the mediator; and
    after forming the reagent mixture, placing the reagent mixture directly on a surface of at least a portion of the working electrode and the counter electrode of the biosensor prior to the introduction of the fluid sample,
    wherein the mixture includes only one enzyme, the oxidizable species is different than the mediator species and the mediator and the oxidizable species have different redox potentials.

11. The method of claim 10 wherein said internal reference is a reduced form of a reversible redox couple that has an equal or higher redox potential than that of said mediator.

12. The method of claim 10 wherein said mediator comprises 3-phenylimino-3H-phenothiazine.

13. The method of claim 12 wherein said internal reference comprises ferrocyanide.

14. The method of claim 10 wherein said internal reference and said mediator are oxidized at a first voltage potential and only said mediator is oxidized at a second voltage potential, said second voltage potential being less than said first voltage potential.

15. The method of claim 10 wherein said internal reference and said mediator are oxidized at a first voltage potential and only said mediator is oxidized at a second voltage potential, said second voltage potential being higher than said first voltage potential.

16. The method of claim 10 wherein said mediator comprises ruthenium hexamine.

17. The method of claim 16 wherein said internal reference comprises ferrocyanide.

18. The method of claim 17 wherein said enzyme comprises glucose oxidase.

19. The method of claim 10 wherein the mediator comprises ferricyanide.

20. The method of claim 19 wherein the internal reference comprises ferrocyanide.

21. A biosensor for determination of an analyte concentration in a test sample comprising:
    a working electrode and a counter electrode;
    a mixture for electrochemical reaction with an analyte, said mixture including an enzyme, a mediator, and an oxidizable species as an internal reference, the oxidizable species being different than the mediator species and having different redox potentials, said mixture being located as a single layer directly on a surface of at least a portion of the working electrode prior to the introduction of the test sample,
    wherein the mixture includes only one enzyme.

22. The biosensor of claim 21 where the only enzyme is glucose oxidase.

23. The biosensor of claim 21 where the mixture includes exactly one mediator and exactly one oxidizable species.

* * * * *

UNITED STATES PATENT AND TRADEMARK OFFICE
CERTIFICATE OF CORRECTION

PATENT NO. : 8,696,880 B2  
APPLICATION NO. : 10/590765  
DATED : April 15, 2014  
INVENTOR(S) : Greg P Beer, Huan-Ping Wu and Kin-Fai Yip Page 1 of 1

It is certified that error appears in the above-identified patent and that said Letters Patent is hereby corrected as shown below:

IN THE SPECIFICATION

In Column 2, Line 60, delete "Iint-ref" and insert -- $I_{int-ref}$ --, therefor In Column 3, Line 65, delete "quantative" and insert -- quantitative --, therefor

IN THE CLAIMS

In Column 14, Line 41, in Claim 22, delete "where" and insert -- wherein --, therefor In Column 14, Line 43, in Claim 23, delete "where" and insert -- wherein --, therefor Signed and Sealed this  
Twenty-first Day of April, 2015

Michelle K. Lee  
*Director of the United States Patent and Trademark Office*